United States Patent [19]

Nakahashi et al.

[11] Patent Number: 4,852,572

[45] Date of Patent: Aug. 1, 1989

[54] MULTI-ELECTRODE TYPE ELECTROCARDIOGRAPHIC ELECTRODE STRUCTURE

[75] Inventors: Yoshinao Nakahashi, Kashiwa; Soichi Osada, Matudo; Chuji Shimizu, Funabashi; Shinshichi Ichida, Tokyo, all of Japan

[73] Assignees: Fukuda Denshi Co., Ltd.; Daido Sangyo Co., Ltd., both of Tokyo, Japan

[21] Appl. No.: 168,089

[22] Filed: Mar. 14, 1988

[30] Foreign Application Priority Data

Mar. 30, 1987 [JP] Japan ............................ 62-47093[U]

[51] Int. Cl.$^4$ ................................................. A61B 5/04
[52] U.S. Cl. .................................................... 128/640
[58] Field of Search .............. 128/639, 640, 644, 798, 128/802, 803

[56] References Cited

U.S. PATENT DOCUMENTS

| | | | |
|---|---|---|---|
| 3,565,059 | 2/1971 | Hauser et al. | 128/640 |
| 3,911,906 | 10/1975 | Reinhold, Jr. | 128/641 |
| 4,067,342 | 1/1978 | Burton | 128/798 |
| 4,082,087 | 4/1978 | Howson | 128/640 |
| 4,141,366 | 2/1979 | Cross, Jr. et al. | 128/640 |
| 4,353,372 | 10/1982 | Ayer | 128/640 |
| 4,522,211 | 6/1985 | Bare et al. | 128/640 |
| 4,583,549 | 4/1986 | Manoli | 128/640 |
| 4,763,660 | 8/1988 | Kroll et al. | 128/640 |

*Primary Examiner*—Lee S. Cohen
*Attorney, Agent, or Firm*—Pollock, Vande Sande & Priddy

[57] ABSTRACT

A multi-electrode type electrocardiographic electrode structure includes a base member made of non-woven cloth, electrode and lead sections formed by using a liquid conductor printed on or impregnating the base member, the electrode section consisting of a plurality of electrodes arranged on the base member, the lead section being connected to the individual electrodes, an electrolyte material provided on the electrodes and serving to reduce the resistance of the skin of a living body, and an insulating adhesive material provided on the base member to alternate with the electrodes for permitting the electrocardiographic electrode structure to be held in close contact with the living body.

4 Claims, 5 Drawing Sheets

MULTI-ELECTRODE TYPE ELECTROCARDIOGRAPHIC ELECTRODE STRUCTURE

BACKGROUND OF THE INVENTION

Field of the Invention

This invention relates to electrocardiographic electrodes for deriving weak voltage from a living body and, more particularly, to a multi-electrode type electrocardiographic electrode structure, which can be easily held in close contact with the living body and also can be inexpensively manufactured.

Prior Art

As is well known in the art, electricity is induced in the living body by the activities of the heart, brain and muscles.

Particularly, electricity generated in the heart is used for the diagnosis of the heart by recording a weak voltage induced on the skin of the living body using an external electrocardiograph. When the electrocardiograph is used, its input section has to be electrically coupled to the living body by having electrocardiographic electrodes in close contact with the skin of the living body.

FIGS. 6 and 7 illustrate a prior art electrocardiographic electrode which is to be held in close contact with the skin of a living body. Reference numeral 1 designates this electrocardiographic electrode.

The electrocardiographic electrode 1 comprises a substantially disk-like base member 2. The base member 2, as shown in FIG. 7, has an adhesive surface 2a so that the electrocardiographic electrode 1 can be held in close contact with the skin M of a living body, as shown in FIG. 8. The base member 2 has a central opening 3.

As shown in FIG. 6, a lead connector 4 is bonded to the upper (or front) surface of the base member 2 to close the opening 3. The lead connector 4 has an upwardly projecting lead coupler 4a, and to its bottom is connected a disk-like electrode 5 made of Ag-AgCl. As shown in FIG. 8, a lead side lead coupler 7 is coupled to the projecting lead coupler 4a. A lead 6 has its one end connected to the lead coupler 7, and its other end is connected to an electrocardiograph (not shown).

To use the electrocardiographic electrode 1 having the above structure for obtaining an electrocardiogram, the base member 2 is bonded to the skin M of the living body, as shown in FIG. 8, and then a recessed portion 7a of the lead side lead coupler 7 is fitted on the projecting lead connector 4a of the lead connector 4 on the side of the electrocardiographic 1, thus coupling the lead side lead coupler 7 to the electrocardiographic electrode 1. In this state, a weak voltage derive from the electrode 5 is coupled through the lead 6 to the electrocardiograph (not shown) for recording.

In an alternative way, the recessed portion 7a of the lead side lead coupler 7 is preliminarily fitted on the projecting lead coupler 4a of the lead connector 4 of the electrocardiographic electrode 1, and then the electrocardiographic electrode 1 with the lead side lead coupler 7 coupled thereto is bonded to the skin M of the living body.

In either one of the ways of use as described above, an electrocardiogram may be obtained. In this use, however the electrocardiographic electrode is used as a consumable, that is, it is discarded when it is removed from the skin after the measurement. Nevertheless, the electrode 5 of the electrocardiographic electrode 1 uses an expensive metal such as Ag-AgCl. Besides, the electrode 5 which leads out a weal voltage directly from the living body, is a separate component from the lead side lead coupler 7 and lead 6 (i.e., lead section) for leading the voltage derived by the electrode 5 to the electrocardiograph. Therefore, complicated assembling is necessary, leading to high cost of manufacture. Particularly, since a plurality of electrocardiographic electrodes is used in combination, the cost problem is substantial. Therefore, development of an electrocardiographic electrode which can be manufactured less expensively has been expected.

In a further aspect, as is seen from FIG. 9, for obtaining an electrocardiogram it is necessary to apply electrocardiographic electrode 1 to the skin M of the living body not only at a single position but at two or more, and recently more than one hundred, positions. With the prior art electrocardiographic electrode 1, in which the electrode 5 and lead 6 are separate components, each lead 6 is coupled to each electrode 1. Since there is a large number of positions, at which an electrode 1 has to be applied to the skin M, therefore, the application of electrodes requires a long time and is very cumbersome. Further, since a large number of leads 6 are wired to the skin M of the living body, there is a possibility that the lead 6 is pulled unconsciously, resulting in detachment of the electrode 1 from the skin M during the electrocardiographic measurement.

Further, for some seriously ill patients electrocardiographic electrodes 1 have to be applied to the back as well. When the patient is lying, he or she will be uncomfortable due to the electrocardiographic electrodes held on the back. Further, prior art electrocardiographic electrodes fail to fit the living body satisfactorily.

Moreover, when the electrode 5 is held in direct close contact with the skin, there is a problem that contact resistance at the skin surface makes the measurement of weak voltage erroneous. To cope with this problem, a water-containing gel member 8, as shown in FIG. 10, is fitted in the opening 3 of the electrocardiographic electrode 1 for reducing the contact resistance of the living body before the electrode is applied to the skin M of the living body as shown in FIG. 8. Where a number of electrocardiographic electrodes 1 are applied at a time, however, the fitting of water-containing gel members 8 in each electrocardiographic electrode 5 is cumbersome and time consuming.

SUMMARY OF THE INVENTION

The present invention seeks to solve the above problems.

According to the invention, there is provided a multi-electrode type electrocardiographic electrode structure, which comprises a base member made of nonwoven cloth, electrode and lead sections formed by using a liquid conductor printed on or impregnating the base member, the electrode section consisting of a plurality of electrodes arranged on the base member, the lead section being connected to the individual electrodes, an electrolyte material provided on the electrodes and serving to reduce the resistance of the skin of a living body, and an insulating adhesive material for permitting the electrocardiographic electrode structure to be held in close contact with the living body.

With the above structure, the electrode section consisting of a plurality of electrocardiographic electrodes is held in contact with the skin of a living body, and the insulating adhesive material on the nonwoven cloth base member is held in contact with the skin, whereby a weak voltage in the living body can be lead out from the electrode section to be led through the lead section to the electrocardiograph for electrocardiographic recording.

DETAILED DESCRIPTION OF THE PREFERRED EMBODIMENT

Now, the construction and operation according to the invention will be described in detail in conjunction with a preferred embodiment thereof.

Figure 1:
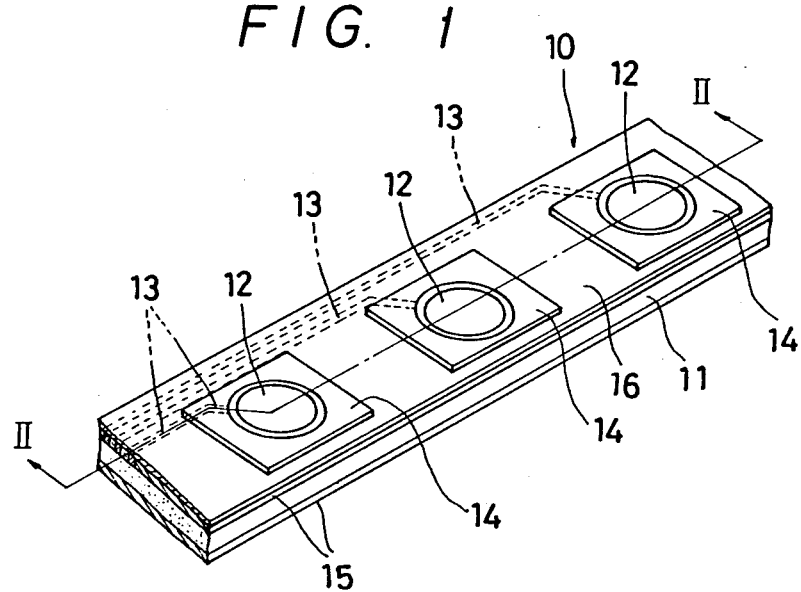
FIG. 1 is a perspective view showing an embodiment of the multi-electrode type electrocardiographic electrode structure according to the invention.
Figure 2:
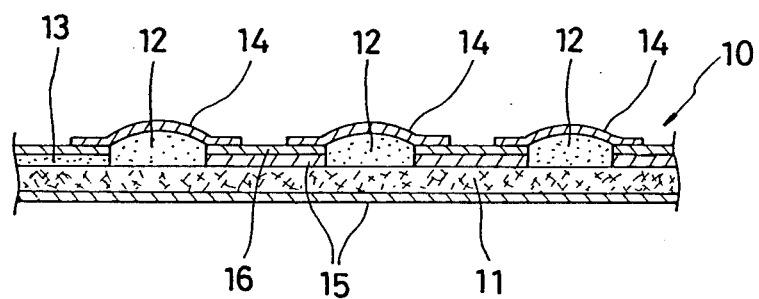
FIG. 2 is a sectional view taken along line II—II in FIG. 1.

FIG. 1 is a perspective view showing an embodiment of the multi-electrode type electrocardiographic electrode structure according to the invention, and FIG. 2 is a sectional view showing the electrocardiographic electrode structure shown in FIG. 1. Reference numeral 10 designates the electrocardiographic electrode structure.

The electrocardiographic electrode 10 has a base member 11. The base member 11 has a rectangular shape, and it is made of non-woven cloth of polyethylene, polyester, polypropyrene, etc.

Reference numeral 12 designates electrodes for leading out a weak voltage from a living body.

The electrodes 12 consists of a conductive ink in close contact with the base member 11. It is either printed on or caused to impregnate the base member 11. It is a conductive material in a paste-like or ink-like form, i.e., in the liquid form, which consists of a conductive metal powder of silver, a mixture of silver and silver chloride, a mixture of silver and conductive graphite or graphite and is prepared by kneading the conductive metal powder together with a resin and a solvent.

Figure 3:
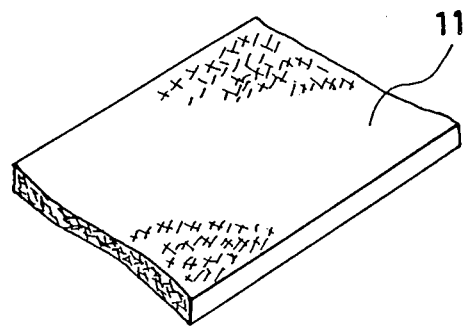
FIG. 3 is a fragmentary perspective view showing a base member made of non-woven cloth.
Figure 4:
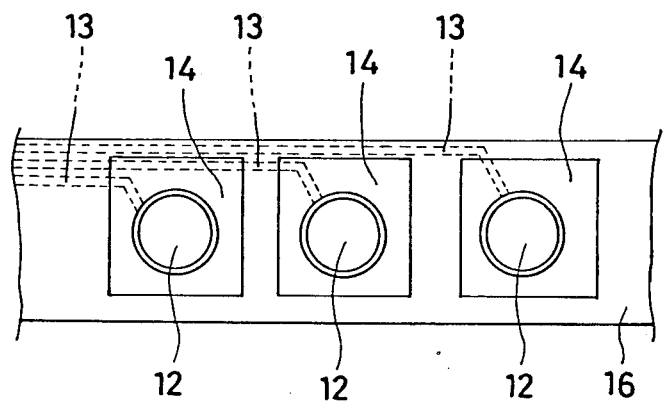
FIG. 4 is a plan view showing the electrocardiographic electrode structure shown in FIG. 1.

The base member 11, on which the conductive ink is printed or which is impregnated by the conductive ink, is made of non-woven cloth. Thus, it is a porous member having an irregular surface, as shown in FIG. 3. It is, therefore, readily permeable to the printed or impregnating conductive ink. This means that the scope of conductive inks available for selection is increased. Further, the base member 11 provides an increased surface area, and the electric resistance with respect to the skin surface is reduced.

Further, the non-woven cloth is felt comfortably by and satisfactory applicable to the skin.

Figure 5:
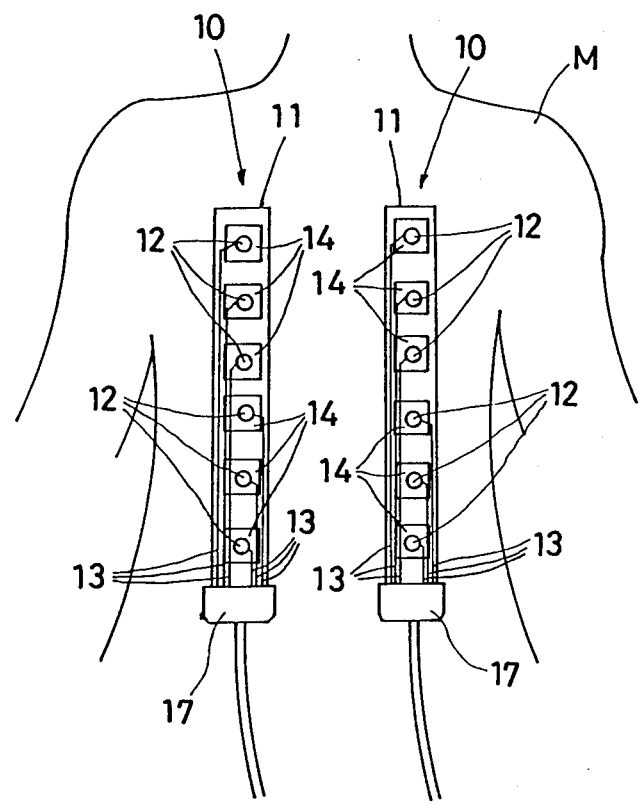
FIG. 5 is a view for explaining the use of the multi-electrode type electrocardiographic electrode structure according to the invention.
Figure 6:
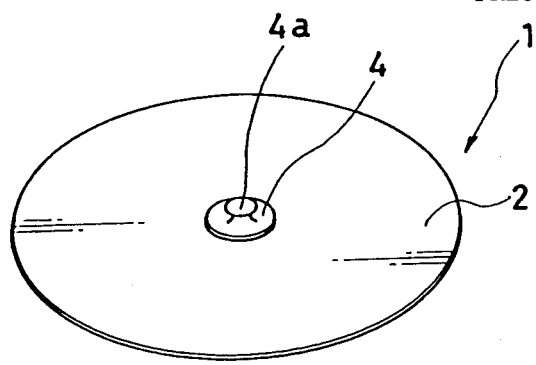
FIGS. 6 to 10 are views for explaining the prior art electrocardiographic electrode.
Figure 7:
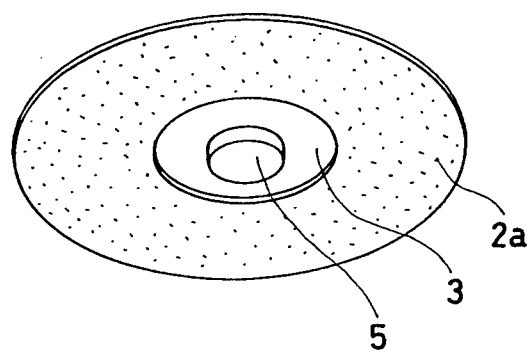
Figure 8:
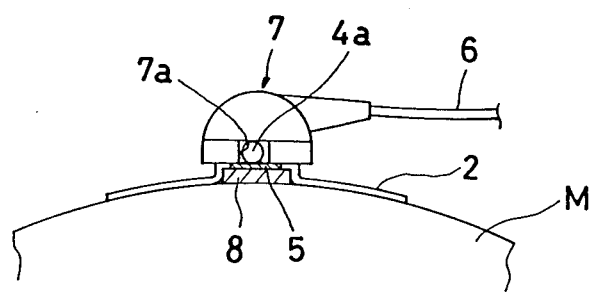
Figure 9:
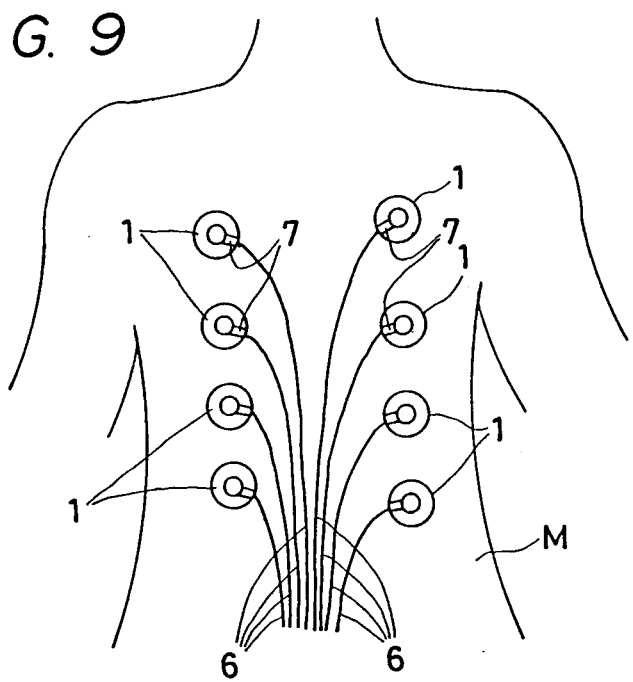
Figure 10:
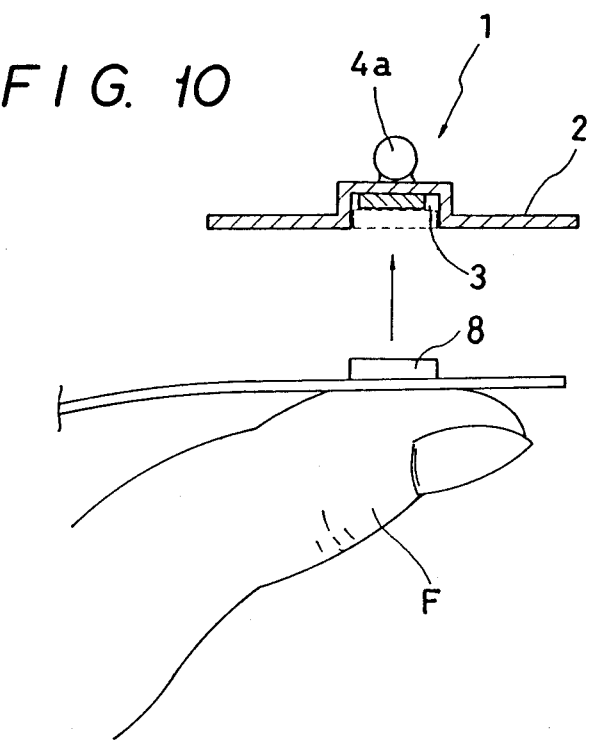

Reference numeral 13 designates leads, which are formed simultaneously with the electrodes 12 from the conductive ink printed on or caused to impregnate the base member 11. These leads 13 extend along the base member 11 and are connected to the respective electrodes 12. Their other ends are connected to a connector 17 (FIG. 5). While in this embodiment three electrodes 12 and three leads 13 are provided, it is possible to provide more than three electrodes and leads.

It is to be understood that the electrodes 12 and leads 13 can be formed simultaneously and integrally by merely printing the conductive ink on or causing it to impregnate the base member 11. That is, the electrodes 12 and leads 13 need not be produced separately, so that the electrocardiographic electrode can be inexpensively manufactured. Further, since the leads 13 are formed in the inside of and do not appear on the base member 11, they will never be pulled unconsciously during the electrocardiographic measurement.

Reference numeral 14 designates an electrolyte material bonded to the electrodes 12. It is a water-containing gel layer made of gelatin, agar, polyacrylamide, etc. It has considerable viscosity, and also it has electric conductivity.

When it is in close contact with the skin of a living body, the electrolyte material 14 leads a weak voltage induced on the skin surface to the electrodes 12. If the electrodes 12 were held in direct close contact with the skin surface, the weak voltage can not be measured accurately due to the contact resistance of the skin surface. For this reason, in the prior art a water-containing gel member serving to reduce the contact resistance of the skin surface is fitted in the electrocardiographic electrode for measuring the weak voltage through the water-containing gel member. However, it is very cumbersome and inefficient to fit the water-containing gell member in the electrocardiographic electrode every time the measurement of weak voltage is done. The electrolyte material 14 is provided in order to eliminate the inconvenience of fitting the water-containing gel member in each electrode 12 that would be otherwise necessary whenever the measurement is done.

Reference numeral 14 designates an insulating material for insulating the leads 13, and numeral 16 an adhesive material for permitting the base member 11 to be applied to the skin M of a living body as shown in FIG. 5.

When using the multi-electrode type electrocardiographic electrode structure 10 as described above, the electrodes 12 are held in contact with the skin M of the living body via the electrolyte material 14, and the adhesive material 16 provided on the base member 11 is held in close contact with the skin M, as shown in FIG. 5. In this state, a weak voltage in the living body is led out from the electrodes 12 through the leads 13 to an electrocardiographic (not shown) for electrocardiographic recording.

In this case, since pluralities of electrodes 12 and leads 13 are provided on a single base member 11, the electrodes 12 with leads 13 may be applied at one time to the skin M of the living body by merely setting the base member 11 in close contact with the skin of the living body. In other words, it is possible to attach electrodes to the skin M in a shorter amount of time.

As has been described in the foregoing, according to the invention electrodes and leads can be formed by merely printing a conductive material in the liquid form on or causing it to impregnate a base member made of non-woven cloth, so that it is possible to manufacture an electrocardiographic electrode structure inexpensively.

Further, since the electrodes and leads are formed integrally by printing or causing impregnation with the liquid conductive material, the efficiency of assembling can be improved, and an electrode having stable electric characteristics can be obtained.

Further, since the base member is provided with a plurality of electrodes and leads each connected to each of the electrodes, a number of electrodes can be applied to the skin of the living body in a short period of time, that is, the efficiency of attaching electrodes can be improved.

Further, since the base member is made of nonwoven cloth, it is very permeable to the liquid conductive material, and it has a satisfactory fitting property with respect to the skin.

Further, since the leads are formed by printing or causing impregnation with the liquid conductive material, they are found inside and not exposed out of the base member. Thus, the possibility of unconscious pulling of leads to result in detachment of the multi-electrode type electrocardiographic electrode structure from the skin of the living body, can be eliminated.

Further, since an electrolyte material serving to reduce the electric resistance of the skin of the living body is provided on the electrodes, there is no need of fitting a water-containing gel member in each electrocardiographic electrode to be set in close contact with the skin. Thus, the multi-electrode type electrocardiographic electrode structure can be used easily, and the operation efficiency can be improved.

What is claimed is:

1. A multi-electrode type electrocardiographic electrode comprising:
    a base member made of non-woven cloth;
    a plurality of electrodes and leads provided on said base member;
    said electrodes and leads being integrally formed by printing on or impregnating said base member within a liquid conductor, said leads being connected to individual electrodes;
    an electrolyte material provided on said electrodes and serving to reduce the resistance of the skin of a living body; and
    an insulating adhesive material layer provided on said base member to alternate with said electrodes whereby said electrocardiographic electrode structure is held in close contact with the skin of the living body.

2. A multi-electrode type electrocardiographic electrode according to claim 2, further comprising an insulating layer connected to said base member at a surface opposite to that including electrode and lead sections.

3. A multi-electrode type electrocardiographic electrode comprising:
    a base member made of non-woven cloth;
    a plurality of electrodes disposed on a first surface of said base member;
    an insulating layer having a plurality of portions with one side disposed on said first surface of said base member said portions alternating with said electrodes;
    a plurality of leads connected to individual electrodes;
    said electrodes and leads being integrally made of a liquid conductor printed on or impregnating said base member;
    an adhesive layer having a first side disposed on an opposite side of each of said portions of said insulating layer;
    a plurality of electrolyte material members, each disposed over one of said electrodes and having ends partially overlapping said adhesive layer with parts of said adhesive layer being exposed for adhering to the skin of a living body.

4. A multi-electrode type electrocardiographic electrode according to claim 3, further comprising an insulating layer connected to a second surface, opposite said first surface of said base member.

* * * * *